United States Patent [19]

Katayama et al.

[11] Patent Number: 5,434,255

[45] Date of Patent: Jul. 18, 1995

[54] PROCESS FOR PURIFYING FRUCTOSE 1,6-DIPHOSPHATE

[75] Inventors: Tatsuo Katayama; Hayato Ishihara; Kenji Okada; Masaaki Onda; Hiroshi Nakajima, all of Kyoto, Japan

[73] Assignee: Unitika Ltd., Hyogo, Japan

[21] Appl. No.: 37,395

[22] Filed: Mar. 26, 1993

[30] Foreign Application Priority Data

Mar. 27, 1992 [JP] Japan .................................. 4-101947

[51] Int. Cl.$^6$ ...................... C07H 11/04; C07H 13/00; C07H 1/06
[52] U.S. Cl. ...................................... 536/117; 536/127
[58] Field of Search ................................ 536/117, 127

[56] References Cited

U.S. PATENT DOCUMENTS

| | | | |
|---|---|---|---|
| 4,530,902 | 7/1985 | Perri et al. | 536/117 |
| 4,575,549 | 3/1986 | Diana et al. | 536/117 |
| 4,787,940 | 11/1988 | Kayane et al. | 536/127 |
| 4,920,049 | 4/1990 | Bisso et al. | 435/105 |
| 5,094,947 | 3/1992 | Nakajima et al. | 536/117 |

OTHER PUBLICATIONS

"Fructose-1, 6-Diphosphoric acid and Fructose-6-Monophosphoric Acid", C. Neuberg et al. Arch Biochem, vol. 3, pp. 33–44, 1943.

"Methods of Enzymatic Analysis" Third Edition, vol. 6, pp. 191–199 and pp. 342–351.

*Primary Examiner*—David A. Redding
*Assistant Examiner*—Everett White
*Attorney, Agent, or Firm*—Sughrue, Mion, Zinn, Macpeak & Seas

[57] ABSTRACT

A process for the purification of fructose 1,6-diphosphate which comprises subjecting a fructose 1,6-diphosphate-containing solution to anion exchange column chromatography to separate fructose 1,6-diphosphate therefrom, and subsequently subjecting the resulting FDP fraction to a desalting treatment, so as to provide a highly purified FDP preparation useful as a pharmaceutical drug and the like in a high yield.

10 Claims, No Drawings

PROCESS FOR PURIFYING FRUCTOSE 1,6-DIPHOSPHATE

FIELD OF THE INVENTION

This invention relates to a process for the purification of fructose 1,6-diphosphate.

BACKGROUND OF THE INVENTION

In general, production of fructose 1,6-diphosphate (hereinafter referred to as "FDP") is effected by synthesizing FDP from:

(1) glucose and phosphoric acid through the Harden-Young type fermentation of yeast cells, or (2) glucose and the like in the presence of acetate kinase-containing cells or extracts thereof, and acetyl phosphate (U.S. Pat. No. 5,094,947, hereby incorporated by reference); and then purifying the thus synthesized FDP by:

(A) forming its precipitate using a calcium or barium salt (*Arch. of Biochem.*, vol. 3, pp. 33–44, 1943), (B) forming its ferric salt (U.S. Pat. No. 4,530,902), or (C) subjecting it to a column separation method (U.S. Pat. No. 4,575,549).

Since FDP purified in accordance with the above process (A) or (B) contains impurities, such as inorganic phosphate and the like in substantial amounts, it is necessary to carry out additional purification procedures when the product is used as a pharmaceutical preparation. In order to purify FDP to a pharmaceutically acceptable level of purity, it had been formerly proposed to use the aforementioned process (C) in which FDP is isolated making use of ion exchange resin chromatography. This process, however, requires a cation exchange treatment as the first step. Since FDP solution becomes acidic by such a treatment, proteinous materials contained as impurities in the solution are denatured and precipitated, and the thus formed precipitate obstructs the passage of the FDP solution through the cation exchange column. Therefore, it is necessary to remove the proteinous impurities from the FDP solution prior to the cation exchange treatment, by denaturing and precipitating the proteinous impurities through heat or hydrochloric acid treatment. However, during such a pretreatment step, FDP is also denatured and lost to some extent, thus lowering the final FDP yield.

SUMMARY OF THE INVENTION

In view of the above, an object of the present invention is to provide a purification process by which fructose 1,6-diphosphate (FDP) can be obtained with a high purity and high yield.

With the aim of overcoming the aforementioned problems involved in the prior art, the inventors of the present invention have conducted intensive studies and found that FDP yield can be improved when purification of an FDP preparation is carried out directly by an anion exchange chromatography, without employing the commonly used first step cation exchange treatment. Moreover, to the inventors' surprise, purified FDP entirely free from impurities can be obtained when a desalting treatment, such as an electro-dialysis or a reverse osmosis, is carried out after the chromatographic treatment, especially in the use of an FDP preparation obtained by one of the prior art synthesizing processes in which FDP is synthesized from glucose in the presence of acetate kinase-containing cells or extracts thereof and acetyl phosphate. The present invention has been accomplished on the basis of these findings.

Particularly, according to the present invention, a process is provided for the purification of FDP which comprises separating FDP from an FDP-containing solution by anion exchange chromatography, and subsequently subjecting the resulting FDP fraction to a desalting treatment.

Other objects and advantages of the present invention will be made apparent in the following description.

DETAILED DESCRIPTION OF THE INVENTION

The present invention is directed to a process for the purification of FDP which comprises separating FDP from an FDP-containing solution by anion exchange chromatography, and subsequently subjecting the resulting FDP fraction to a desalting treatment.

The term "anion exchange chromatography treatment" as used herein means that a crude FDP solution to be purified is adsorbed on an anion exchange resin, and the adsorbed FDP is recovered by eluting it with an eluant, such as an inorganic salt-containing aqueous solution or the like.

The term "desalting treatment" as used herein means a treatment for the removal of inorganic salts contained in the eluted and recovered FDP fraction.

Any type of crude FDP solution can be applied to the purification process of the present invention, but a solution of FDP synthesized by the aforementioned process (2) is particularly desirable. The crude FDP solution as it is may be subjected to anion exchange chromatography treatment. Alternatively, the crude FDP solution may be subjected to anion exchange chromatography treatment after removing phosphate impurities by precipitating them using a precipitant, such as barium chloride, zinc chloride, magnesium chloride, calcium chloride or the like, and/or removing proteinous impurities by means of ultrafiltration.

Any type of known anion exchange resins which are capable of adsorbing FDP may be used in the anion exchange chromatography treatment, such as Dowex SAR (Muromachi Kagaku Kogyo Co., Ltd.), Amberlite IRA-400 (Japan Organo Co. Ltd.), Diaion SA-20A (Mitsubishi Kasei Corp.) and the like. These resins are used by packing each of them in a column made of glass, steel or the like.

The concentration of the FDP solution to be subjected to the anion exchange chromatography treatment may be 1M or less, preferably 100 mM or less, to avoid leakage at the time of its application, more preferably 10 mM or less. The liquid flow rate in the packed column may be controlled to 20 m/hr or less, preferably a 6 m/hr or less, more preferably at around 2 m/hr.

FDP thus adsorbed to the resin is then recovered by its elution with an aqueous solution of an inorganic salt, such as sodium chloride or the like. In this instance, an organic solvent, such as ethanol or the like, may be added to the eluting solution. FDP is separated from impurities such as phosphoric acid, acetic acid, and the like, by setting a gradient of salt density at the time of the elution (gradient technique) or using two or more eluting solutions having different salt concentrations (stepwise technique).

Next, inorganic salts in the thus obtained FDP fraction are removed by a desalting treatment, making use of an electrodialysis membrane or a reverse osmosis membrane. Any type of membrane may be used in this treatment, provided that it is permeable to the inorganic salts used in the elution, but not to FDP. Examples of the electrodialysis membrane include hydrocarbon-based high polymer materials such as AC-110 (Asahi Chemical Co., Ltd.) and the like, as well as fluorine-containing hydrocarbon-based high polymer materials, and examples of the reverse osmosis membrane include polyamide materials, such as SU-210S (Toray Co., Ltd.) and the like.

According to the present invention, a high purity FDP preparation can be obtained with a high yield by separating it from an FDP-containing solution through the anion exchange chromatography treatment, and subsequently subjecting the resulting FDP fraction to the desalting treatment, thus rendering possible industrial scale production of FDP for pharmaceutical use.

The following examples are provided to further illustrate the present invention. It is to be understood, however, that the examples are for purpose of illustration only and are not intended as a definition of the limits of the invention.

REFERENCE EXAMPLE 1

A 365 ml aqueous solution containing each 45 kilounits of acetate kinase, glucokinase, phosphofructokinase and phosphoglucose isomerase (produced by Unitika Ltd.) was added to a 50-liter reaction vessel containing 16 liters of 10 mM Tris-HCl buffer solution at pH 7.6 containing 6.0 mol of glucose, 30 mmol of ATP, 150 mmol of ammonium sulfate, and 600 mmol of $MgCl_2$ at 30° C. The temperature of the reaction vessel was maintained at 30° C. throughout the reaction. To this 16 liters of reaction solution, 2 liters of aqueous solution of approximately 900 mM of sodium acetyl phosphate prepared from phosphoric acid, acetic anhydride, and sodium bicarbonate was added to start the synthesis of fructose-1,6-diphosphate. When 1, 2, 4, 6 and 8 hours elapsed after initiation of the reaction, each 2 liters of the acetyl phosphate solution was added to the reaction solution in the reaction vessel. The pH lowering that accompanied the addition of the acetyl phosphate was compensated for by the addition of a sufficient amount of a 24% sodium hydroxide aqueous solution to maintain the pH at 7.6. The reaction was stopped after 24 hours when 12 liters, total, of acetyl phosphate solution had been added.

The final volume of the solution was 30 liters and contained 134 mM of fructose-1,6-diphosphate, 88 mM of phosphoric acid, and 393 mM acetic acid. The yield of fructose-1,6-diphosphate from the glucose substrate was 67%.

REFERENCE EXAMPLE 2

*Bacillus stearothermophilus* NCA-1503 strain (ATCC 29609) was inoculated into 500 liters of a culture medium containing 0.35% of glucose, 0.30% of yeast extract, 0.10% of peptone, 0.10% of $KH_2PO_4$, 0.10% of $Na_2HPO_4 \cdot 12H_2O$, 0.05% of $MgSO_4 \cdot 7H_2O$, 5 mg/l of ferrous sulfate, 5 mg/l of calcium hydroxide, 1 mg/l of manganese sulfate, and 1 mg/l of sodium molybdate. The pH of the culture medium was adjusted with 4N sodium hydroxide to the range of from 6.8 to 7.2 at a temperature of from 58° to 60° C. The cultivation method was repeated several times. The microorganisms were recovered from the culture medium by centrifugation, and stored frozen.

9.9 kg of frozen microorganisms were suspended in 2 liters of a 25 mM-potassium phosphate buffer solution (pH: 7.6) containing 1M of glucose and 4 mM of EDTA. The suspension was maintained at a temperature of 40° C. After standing for 2 hours, the microorganisms were crushed, and the acetate kinase activity was determined to be 16,900 units per liter.

It was added to a 500-liter reaction vessel containing 150 liters of 32 mM imidazole-HCl buffer solution at pH 8.0 containing 48 mol of glucose, 0.24 mol of ATP, 1.2 mol of ammonium sulfate, and 4.8 mol of $MgCl_2$ at 30° C. The temperature of the reaction vessel was maintained at 30° C. throughout the reaction. To this 186 liters of reaction solution, 24 liters of aqueous solution of approximately 800 mM of sodium acetyl phosphate prepared from phosphoric acid, acetic anhydride, and sodium bicarbonate was added to start the synthesis of fructose-1,6-diphosphate. When 1, 2, 4, 6 and 8 hours elapsed after initiation of the reaction, each 24 liters of the acetyl phosphate solution was added to the reaction solution in the reaction vessel. The pH lowering that accompanied the addition of the acetyl phosphate was compensated for by the addition of a sufficient amount of a 24% sodium hydroxide aqueous solution to maintain the pH at 7.9-8.0. The reaction was stopped after about 24 hours when 144 liters, total, of acetyl phosphate solution had been added.

The final volume of the solution was 380 liters and contained 109 mM of fructose-1,6-diphosphate, 121 mM of phosphoric acid, and 531 mM acetic acid. The yield of fructose-1,6-diphosphate from the glucose substrate was 86%.

EXAMPLE 1

A 29 g portion of zinc chloride was added to 2 liters of a solution containing 134 mM FDP, 88 mM phosphoric acid and 393 mM acetic acid obtained in Reference Example 1, and the mixture was stirred while its pH level was controlled at 8.0 with 24% sodium hydroxide solution. After removing the formed precipitate by filtration, the resulting mother liquid (FDP concentration: 102 mM) was diluted 4.9 times with water, and a 2.73 liter portion of the diluted solution (FDP concentration, 20.8 mM) was passed through a column (h=5 cm) packed with 100 ml of an anion exchange resin Dowex SAR (Muromachi Kagaku Kogyo Co., Ltd.) at a liquid flow rate of 0.54 m/hr. Of the 56.8 mmol of FDP applied to the column, 28.5 mmol were adsorbed to the resin and the remaining 28.3 mmol were recovered as non-adsorbed fractions. Next, 100 ml of ion exchanged water and 2 liters of 0.04M NaCl aqueous solution which had been adjusted to pH 2 with hydrochloric acid were passed through the column in order to wash out acetic acid and phosphoric acid, and the FDP retained by the column was eluted with 2 liters of 0.4M NaCl solution which had been adjusted to pH 2 with hydrochloric acid. The FDP fractions thus recovered were subjected to desalting using a Micro Acylizer (Asahi Chemical Co., Ltd.) to obtain an aqueous solution of FDP sodium salt containing no impurities. As a result, FDP was recovered in an amount of 26.0 mmol with a recovery yield of 69%.

EXAMPLE 2

A 7.0 kg portion of zinc chloride was added to 380 liters of a solution containing 109 mM FDP, 121 mM phosphoric acid and 531 mM acetic acid obtained in Reference Example 2, and the mixture was stirred while its pH level was controlled at 8.0 with 24% sodium hydroxide solution. After removing the formed precipitate by filtration, the resulting mother liquid (FDP concentration: 95 mM) was passed through ultrafilter. A 250 liter portion of the ultrafiltered liquid (430 liters, FDP concentration: 78 mM) was diluted 8 times with water, and the thus diluted solution (FDP concentration, 9.75 mM) was passed through a column (h=47 cm) packed with 85 liters of an anion exchange resin Dowex SAR (Muromachi Kagaku Kogyo Co., Ltd.) at a liquid flow rate of 1.66 m/hr. All of the 19.5 mol FDP applied to the column were adsorbed to the resin. Next, 2,000 liters of 0.04M NaCl aqueous solution which had been adjusted to pH 2 with hydrochloric acid were passed through the column to wash out acetic acid and phosphoric acid, and the FDP retained by the column was eluted with 0.4M NaCl solution which had been adjusted to pH 2 with hydrochloric acid. The FDP fractions thus recovered (1,250 liters) were subjected to desalting concentration using a reverse osmosis membrane (SU-210S, Toray Co., Ltd.) to obtain an aqueous solution of FDP sodium salt containing no impurities. As a result, FDP was recovered in an amount of 14.9 mmol with a recovery yield of 62%.

The FDP sodium salt solution obtained in Example 2 was subjected to freeze drying to obtain a powder sample having the following composition. In this instance, inorganic phosphorus was determined using Phospher C test WAKO (Wako Pure Chemical Industries Ltd.) and sodium chloride was determined using Chloride test WAKO (Wako Pure Chemical Industries Ltd.). Moisture content was determined by the Karl Fischer's method, and FDP, G6P and F6P were determined in accordance with the procedure disclosed in *Methods of Enzymatic Analysis* (Verlag Chemie, Weinheim).

As a result, it was found that the FDP powder obtained by the purification process of the present invention has much higher purity than that of a commercial pharmaceutical FDP preparation for injection use which has been put on the overseas market Esafosfina® by Biomedica Foscama Industria Chimico-Pharmaceutica S.p.A.

|  | FDP Powder of Example 2 (% by weight) | Commercial Pharmaceutical FDP Preparation for Injection Use (Biomedica Foscama Industria Chimico-Pharmaceutica S.p.A.) (% by weight) |
| --- | --- | --- |
| (FDP)HNa$_3$ | 91.9 | 85.6 |
| G6P, F6P | 0.4 | 0.8 |
| Inorganic phosphorus | 0.1 | 3.6 |
| Sodium chloride | 0.1 | 2.3 |
| Moisture content | 7.4 | 7.9 |

Thus, the present invention provides a process for the purification of FDP by which a highly pure FDP preparation useful as a pharmaceutical drug and the like can be obtained with a high yield through simple steps.

Although some preferred embodiments have been described, many modifications and variations may be made thereto in the light of the above teachings. It is to be understood therefore that within the scope of the following claims, the invention may be practiced otherwise than as specifically described.

What is claimed is:

1. A process for purifying fructose 1,6-diphosphate comprising the steps of:
   (A) adding a fructose 1,6-diphosphate-containing solution to an anion exchange column so as to absorb fructose 1,6-diphosphate onto said column;
   (B) eluting said absorbed fructose 1,6-diphosphate from said anion exchange column to obtain a fructose 1,6-diphosphate fraction; and then
   (C) subjecting the fructose 1,6-diphosphate fraction to a desalting treatment using a reverse osmosis membrane;
   so as to provide purified fructose 1,6-diphosphate.

2. The process for purifying fructose 1,6-diphosphate according to claim 1, wherein said fructose 1,6-diphosphate-containing solution to be added to the anion exchange column has a concentration of 1M or less.

3. The process for purifying fructose 1,6-diphosphate according to claim 2, wherein said fructose 1,6-diphosphate-containing solution to be added to the anion exchange column has a concentration of 100 mM or less.

4. The process for purifying fructose 1,6-diphosphate according to claim 3, wherein said fructose 1,6-diphosphate-containing solution to be added to the anion exchange column has a concentration of 10 mM or less.

5. The process for purifying fructose 1,6-diphosphate according to claim 1, wherein passage of the step (A) solution through said anion exchange column is effected at a liquid flow rate of 20 m/hr or less.

6. The process for purifying fructose 1,6-diphosphate according to claim 5, wherein passage of the step (A) solution through said anion exchange column is effected at a liquid flow rate of 6 m/hr or less.

7. The process for purifying fructose 1,6-diphosphate according to claim 6, wherein passage of the step (A) solution through said anion exchange column is effected at a liquid flow rate of around 2 m/hr.

8. The process for purifying fructose 1,6-diphosphate according to claim 1, wherein said absorbed fructose 1,6-diphosphate is eluted from the anion exchange column through the use of an inorganic salt aqueous solution.

9. The process for purifying fructose 1,6-diphosphate according to claim 8, wherein said inorganic salt aqueous solution is a sodium chloride aqueous solution.

10. The process for purifying fructose 1,6-diphosphate according to claim 1, wherein prior to step (A), said fructose 1,6-diphosphate-containing solution is initially purified to remove (i) phosphate impurities by means of a precipitant selected from the group consisting of barium chloride, zinc chloride, magnesium chloride, and calcium chloride, and (ii) proteinous impurities by means of ultrafiltration.

* * * * *